United States Patent [19]

Weisman et al.

[11] Patent Number: 4,469,746

[45] Date of Patent: Sep. 4, 1984

[54] SILICA COATED ABSORBENT FIBERS

[75] Inventors: Paul T. Weisman, Fairfield; Herbert L. Retzsch, Cincinnati, both of Ohio

[73] Assignee: The Procter & Gamble Company, Cincinnati, Ohio

[21] Appl. No.: 383,685

[22] Filed: Jun. 1, 1982

[51] Int. Cl.$^3$ .......................... D04H 1/58; B32B 5/16
[52] U.S. Cl. ................................. 428/289; 427/397.7; 427/402; 427/407.1; 427/430.1; 428/283; 428/375; 428/451; 428/452; 428/913
[58] Field of Search .............. 428/289, 375, 378, 451, 428/452, 913, 283, 221; 427/397.7, 397.8, 402, 407.1, 430.1

[56] References Cited

U.S. PATENT DOCUMENTS

| | | | |
|---|---|---|---|
| 2,443,512 | 6/1948 | Powers | 19/66 R |
| 2,658,835 | 11/1953 | Wymbs | 106/287.22 |
| 3,381,688 | 5/1968 | Satas | 604/368 |
| 3,720,539 | 3/1973 | Seibel et al. | 427/393.5 |
| 3,775,141 | 11/1973 | Weidman | 501/95 |
| 4,049,764 | 9/1977 | Sigl et al. | 264/178 F |
| 4,307,143 | 12/1981 | Meitner | 252/91 |
| 4,311,553 | 1/1982 | Akerlund et al. | 162/23 |

Primary Examiner—William J. Van Balen
Attorney, Agent, or Firm—Jacobus C. Rasser; Steven J. Goldstein; Jack D. Schaeffer

[57] ABSTRACT

Fibrous webs comprising fibers coated with a continuous film comprising silica have excellent absorbent and wicking properties. The fibers themselves may be hydrophilic (e.g., cellulose) or hydrophobic (e.g., a polyolefin or a polyester).

15 Claims, No Drawings

SILICA COATED ABSORBENT FIBERS

TECHNICAL FIELD

This invention relates to a method to improve the hydrophilic properties of absorbent webs. Absorbent webs are extensively used in a wide variety of products, ranging from disposable towel sheets to sanitary napkins and from disposable diapers to surgical sponges. All these applications involve the absorption of water or aqueous liquids (urine, blood, lymph, spills of coffee, tea, milk, etc.). The absorbent webs used in such products therefore must be able to absorb large quantities of aqueous liquids. The webs must also have good wicking properties, i.e., water must be readily taken up and spread throughout the web.

Webs having superior absorption capacity are the subject of copending application, Early et al. Ser. No. 383,686, filed June 1, 1982.

The wicking properties of an absorbent web are largely determined by its hydrophilicity. Cellulose fibers are reasonably hydrophilic and relatively inexpensive and are by far the most extensively used fibers for absorbent webs. Wood pulp, which is almost invariably used as a source of such cellulose fibers, contains hydrophobic materials like fatty acids and triglycerides, generally referred to as "pitch". These hydrophobic materials adversely affect the hydrophilicity of the fibers. Methods have been developed to remove these hydrophobes (generally repeated washings with alkali, or solvent extraction), but it is doubtful whether all of these materials can be removed by such treatments. In any event, the best obtainable hydrophilicity is that of clean cellulose. It would be desirable to develop fibers that can form webs which have a greater hydrophilicity and/or better wicking properties than conventional cellulose for fiber webs.

Manmade thermoplastic fibers have the advantage that they can be manufactured in any desirable fiber diameter. This is particularly important in view of the discovery that certain webs comprising fibers which have a diameter of less than 15 microns possess an unusually high absorption capacity. Thermoplastic fibers can readily be made in diameters of less than 15 microns, whereas the reduction of the diameter of cellulose fibers to values below 15 microns involves extensive working under high shear conditions, as disclosed in the above cited copending application, Early et al Ser. No. 383,686 filed June 1, 1982. However, the hydrophilicity of thermoplastic fibers is at best far inferior to that of cellulose fibers. Many thermoplastic fibers (e.g., the polyolefins) are virtually hydrophobic.

The physical process of wetting is described by wetting equations such as the Washburn equation or the Young-Laplace equation. The dominant term in these equations is the product of the liquid/vapor interface tension ($\gamma_{LV}$) and the cosine of the advancing contact angle ($\cos \theta$). Removing pitch from cellulose typically minimizes $\theta$, and thus maximizes $\cos \theta$, without changing $\gamma_{LV}$. By "hydrophilizing" herein is meant modification of a solid surface (e.g., a fiber surface) resulting in a smaller advancing contact angle $\theta$, without changing the value of $\gamma_{LV}$.

Attempts to increase the hydrophilicity of cellulose fibers have thus far been limited to improved processes for removing pitch from the wood pulp. At best the hydrophilicity of such fibers will be that of clean cellulose. Methods to make such fibers more hydrophilic than cellulose have not been reported.

Thus far, no convenient methods for hydrophilizing thermoplastic fiber webs are available. Impregnating such webs with a surfactant results in a certain degree of wettability. The surfactant dissolves in the fluid to be absorbed, thus lowering the liquid/solid interface tension, and hence the advancing contact angle $\theta$. At the same time, however, the value of $\gamma_{LV}$ is also lowered, which limits the wicking properties which may be obtained with such a surfactant treatment. Moreover, the lower surface tension of the fluid adversely affects the partitioning capabilities of the absorbent web. It is desirable, therefore, to hydrophilize the fibers rather than to attempt to modify the surface tension of the fluid to be absorbed.

It is therefore an object of this invention to provide a method to improve the hydrophilicity of conventionally processed cellulose fibers. It is a further object of this invention to provide a method for hydrophilizing thermoplastic fibers. It is a still further object of this invention to provide highly absorbent structures having improved liquid distribution properties.

BACKGROUND ART

Numerous attempts to improve the wicking properties and wet strength properties of highly absorbent web structures have been described in the art.

Sigl, et al., U.S. Pat. No. 4,049,764, issued Sept. 20, 1977, disclose an extrusion process for the formation of cellulose fiber webs. Highly absorbent and rapidly wicking filaments and web structures are formed when the extrudate is treated prior to extrusion with a solvent like acetone.

U.S. Pat. No. 4,307,143, issued Dec. 22, 1981, to Meitner, discloses wetting agents suitable for making polypropylene webs oil and water absorbent. The wetting agents are selected from the group consisting of dioctylester of sodium sulfosuccinic acid and isooctyl phenyl-polyethoxy ethanol.

Silica has been proposed for modifying the properties of fibers and sheet like materials. For example, U.S. Pat. No. 2,443,512, issued June 15, 1948 to Powers, discloses the use of silica sols for improving the manipulative characteristics of textile fibers. The fibers are simply dipped in a silica aquasol and subsequently dried. This method of treatment is not capable of permanently modifying the fiber properties, but the silica particles stay on the fiber surface long enough to improve breaking strength and reduce slippage during subsequent processing (i.e., weaving). Colloidal silica has further been proposed for treating non-fibrous, non-porous cellulose sheets to prevent them from sticking together (U.S. Pat. No. 2,658,835, issued Nov. 10, 1953 to Wymbs). The sheets are simply soaked in a bath containing colloidal silica, and subsequently dried. A colloidal silica deposit in wound dressings may act to improve the strike through characteristics of the pad, as described in U.S. Pat. No. 3,381,688, issued May 7, 1968 to Satas. Since the silica is simply sprayed on, its substantivity to the absorbent web is poor. Application of the silica is therefore limited to these parts of the dressing which do not come into contact with the skin or the wound.

For applications where substantivity of the silica coating is indispensable, relatively complicated methods of coating have been developed. For example, where silica is used as a binder in fibrous refractory materials it has been suggested to use colloidal silica particles having a positive surface charge, to flocculate the silica onto the refractory fibers by negatively charged clay minerals, to subsequently impregnate the material with negatively charged colloidal silica, and bake at 200° C. or higher (U.S. Pat. No. 3,775,141, issued Nov. 27, 1973 to Weidman). Baking is, of course, not possible where the fiber or sheet is a polymer like polypropylene. Substantivity of a silica or silicate comprising hydrophilic coating for polyester may be achieved by the use of complicated chemical mixtures. See, for example, U.S. Pat. No. 3,720,539, issued Mar. 13, 1973 to Seibel, et al., which discloses pretreatment of the polyester article with an aqueous solution of trichloroacetic acid, polyvinyl alcohol and a cleansing agent, and subsequent treatment with a solution comprising aluminum silicate, polyvinyl alcohol, polyvinyl acetate and a melamine-formaldehyde resin. As exemplified by the references cited herein, prior art methods of forming substantive silica coatings involve complex processes. With the process of the present invention silica coated fibers can be made by a simple process. Absorbent webs made of such fibers have excellent absorption and wicking properties.

DETAILED DESCRIPTION OF THE INVENTION

This invention relates to hydrophilic absorbent fibrous webs comprising fibers which are coated with a continuous film comprising silica. The fibrous webs of this invention have wicking and absorption properties which are far superior to the properties of conventional absorbent webs, which makes them particularly suitable for use in various products such as diapers, towel sheets, surgical sponges, tampons, and the like.

The fibers themselves may be wettable or non-wettable by aqueous effluents in the untreated states. Wood pulp fibers which are abundantly available at low cost are particularly suitable wettable fibers for use in the fibrous absorbent webs of the present invention. It has surprisingly been found that coating fibers with a continuous film comprising silica results in a marked improvement of absorption and wicking properties of webs made with such fibers. By wood pulp fibers herein is meant fibers made from wood chips by one of the variety of chemical, mechanical, thermo mechanical and chemi-thermo mechanical processes available. Since the relative hydrophilicity of the untreated fibers is dependent upon the wood species and upon the process, different fibers benefit from the treatments of the present invention to varying degrees. Thus, for example, a northern hardwood sulphite pulp benefits more than a southern softwood Kraft pulp.

Webs may be formed which consist essentially of fibers coated with a continuous film comprising silica. It is also possible to form wegs by mixing fibers which are coated with a continuous film comprising silica with untreated fibers. For example, the strength of a southern softwood Kraft pulp fiber web may be increased by blending in chemithermo mechanical fibers. The relatively poor hydrophilicity of the latter fibers can be off-set by coating them with a continuous film comprising silica prior to blending with the southern softwood Kraft pulp fibers. Similarly, coated thermoplastic fibers can be blended with untreated cellulose fibers prior to formation of the web.

Silica may be either negatively charged or positively charged. When positively charged or negatively charged silica is used in conjunction with cellulose fibers, the silica is essentially the only component of the continuous film coating the fiber. When positively charged silica is used for coating thermoplastic fibers, the continuous film must contain a crosslinkable cationic polyelectrolyte as a second constituent. But negatively charged silica can be the sole constituent of a continuous film coating when the fiber is of a thermoplastic material.

Negatively charged silica suitable for use in the present invention is commercially available in the form of aquasols. Typical processes for preparing these silica aquasols are those such as disclosed in Alexander and Iler, U.S. Pat. No. 2,892,797; Bechtold and Synder, U.S. Pat. No. 2,574,902; Rule, U.S. Pat. No. 2,577,485; and White, U.S. Pat. No. 2,285,477, all of which are incorporated herein by reference. The average colloidal silica particle size may range from about 3 nanometers to about 150 micrometers, preferably from about 3 nanometers to about 50 nanometers. Ordinarily, the sols are stabilized by the presence of a small amount of alkali such as sodium hydroxide or ammonium hydroxide. Commercially available silica aquasols may vary in silica content (from about 20% to about 50% $SiO_2$) and in pH (from about 8 to about 10).

Aquasols of positively charged silica can be made by depositing alumina on the surface of colloidal silica particles. This may be achieved by treating an aquasol of negatively charged silica with aluminum acetate, aluminum chloride, or an alkali metal aluminate. Typical processes for preparing these positively charged silica sols are disclosed by Moore, U.S. Pat. No. 3,620,978; Moore, U.S. Pat. No. 3,956,171; Moore, U.S. Pat. No. 3,719,607; Moore, U.S. Pat. No. 3,745,126; and Bergna, U.S. Pat. No. 4,217,240, all of which are incorporated herein by reference. The aluminum treatment results in aluminum:silica ratios at the surface of the colloidal particles ranging from about 1:19 to about 4:1. Preferred for use herein are aluminum:surface silica ratios of from about 1:2 to about 2:1. The sol is stabilized by a slightly acidic pH which may be achieved by adding small amounts of an acid, e.g., acetic acid, or by passing the sol through a bed of a strongly acidic ion exchange resin.

COATED THERMOPLASTIC FIBERS

An important embodiment of the present invention utilizes thermoplastic fibers coated with a continuous film comprising silica. Such fibers are usually hydrophobic or marginally hydrophilic. But when coated in accordance with the present invention, these fibers are highly hydrophilic. Absorbent webs formed with these fibers have excellent absorption and wicking properties with respect to aqueous fluids.

Virtually any thermoplastic polymer is suitable for use herein, in particular the polyolefins, the polyesters, the polyamides and the polyvinyls. Suitable examples are polyethylene, polypropylene (both of which are polyolefins); poly(ethylene terephtalate) (a polyester); nylon 6,6 (a polyamide); and polyvinylchloride (a polyvinyl). For cost reasons polyethylene, polypropylene and poly(ethylene terephtalate) are preferred.

Techniques of forming polymer fibers are well known in the art and disclosed in, for example, B. P. Corbman's "Textiles: Fiber to Fabric", fifth edition, 1975, McGraw Hill, New York, incorporated herein by reference. Of particular interest is the so-called biconstituent spinning process disclosed in Corbman at page 62. This technique produces microfibers (diameter less than 15 microns) which are particularly suitable for the formation of highly absorbent webs. Microfibers may also be formed in the melt-blowing process described in U.S. Pat. No. 3,755,527, issued to Keller et al., the disclosure of which is incorporated herein by reference.

The thermoplastic fibers can be formed into a web by air-laying or solvent laying. The wet strength of the web may be increased by heat fusion, whereby the web is heated to a temperature at which the fibers become soft.

The thermoplastic webs are subsequently hydrophilized by depositing the silica comprising coating onto the fibers. It is essential that this coating be present in the form of a continuous film. The presence of hydrophobic polymer at the surface of the fiber not only negatively affects the absorption capacity of the web, but also slows down or stops the advance of liquid on the fiber surface and is therefore detrimental to the web's wicking properties.

Since thermoplastic fibrous webs are hydrophobic, such webs are not wetted by silica aquasols. Silica aquasols may be made to wet the webs by adding surfactants. An undesirable effect of this approach is that some of the surfactant is deposited on the fiber surface along with the silica. When webs made of such fibers are used for the absorption of aqueous liquids, the surfactant dissolves in the liquid to be absorbed. This lowers the liquid/vapor interface tension and thereby negatively affects the wicking and partitioning of the liquid into the web. The use of surfactants is therefore undesirable for the purpose of the present invention and should be avoided.

Thermoplastic webs can be wetted with a silica aquasol by immersing the web in the sol under reduced pressure. In this process the web is contacted with the sol in an airtight vessel. Subsequently, the pressure in the vessel is reduced to less than 10 cm Hg (less than about $1.3 \times 10^4$ N/m$^2$), preferably less than about 2 cm Hg (less than about $2.7 \times 10^3$ N/m$^2$). This pressure is maintained for about 5 to about 10 minutes, during which air escapes from the web and the sol enters the pores. Then the vessel is put back at atmospheric pressure. It is advantageous, but not necessary, to repeat this vacuum treatment at least once. When the web is treated with negatively charged silica, the next step is draining of the web and drying. Although drying conditions are not critical to the process of the present invention, it is advantageous to dry the web in air at about 65° C. When the web is treated with positively charged silica, the next step after vacuum immersion is immersion in an aqueous solution of a crosslinkable cationic polyelectrolyte, as described below.

The concentration of the silica aquasol, whether the silica is positively charged or negatively charged, is from about 0.001% to about 10%. At concentrations below 0.001%, the aquasol does not readily wet the web, even when under reduced pressure. When the concentration exceeds about 10%, more silica is deposited on the fiber than is necessary to cover the surface of the fiber with a continuous coating. This may result in blocking of pores with a small diameter. Preferably, the concentration of the silica aquasol is in the range of from about 0.005% to about 2%.

Impregnation of the web with silica sol can also be obtained by so-called padding, whereby the web is contacted with the silica sol by e.g. immersion or by spraying, and is subsequently squeezed between rolls. Padding requires a higher silica sol concentration than the vacuum immersion technique described above: from about 0.5% for slowly operated padding machines to about 30% for fast operated padding machines. The nip pressure should be such as to ensure complete wetting of the web, as will be apparent to someone skilled in the art. Several types of padding machines and their operation are described by Dennis E. Wood in *Nonwovens & Disposable Soft Goods*, Vol. 5, #4, pp. 25-6, 38-9; Vol. 5 #5., pp. 14-6, 18, 20; Vol. 5 #6, pp. 24-6, 28, all of which are incorporated herein by reference.

The pH value of the silica aquasol, whether the silica is positively charged or negatively charged, must be in the range of from about 1 to about 5. When the pH of the aquasol is above about 5, the silica deposited on the fiber is not present in the form of a continuous coating. Webs made with such fibers have poor absorption and wicking properties. When the pH of the aquasol is less than about 1, significant amounts of acidic material are deposited on the fiber. This may cause irritation if the web is to be used in contact with skin. The preferred pH range is from about 3 to about 4.

The effect of the pH on the deposition of continuous films of negatively charged silica was established as follows. Pieces of polyethylene terephtalate film (MYLAR) were submerged in a 0.1% negatively charged silica, particle size 7-8 nm (LUDOX SM from DuPont deNemours) for 20 minutes. The polyester film samples were removed, rinsed with distilled water and dried under ambient conditions. A drop of distilled water was put on the dry film and its initial contact angle measured. The smaller the initial contact angle, the better the wetting of the film.

| Silica pH | Contact angle |
|---|---|
| 9.6 | 71 ± 5 |
| 7 | 69 ± 4 |
| 6 | 72 ± 1 |
| 5 | 72 ± 2 |
| 4 | 50 ± 2 |
| 3 | 42 ± 3 |
| 2 | 28 ± 4 |

The data demonstrate that negatively charged silica must be deposited at pH values below 5 in order to achieve improved wetting of thermoplastic surfaces.

When negatively charged silica is used in the practice of this invention, an electrolyte must be added to the aquasol. The function of the electrolyte is to impart a certain ionic strength to the sol. Any soluble salt is suitable for this purpose. Examples are sodium chloride, potassium chloride, calcium chloride, calcium carbonate, magnesium chloride, sodium sulfate, potassium sulfate, ammonium chloride, ammonium sulfate, and the like. The amount of electrolyte is such as to provide an ionic strength of from about 0.003 to about 0.45. Ionic strength is defined as the summation over all different ions present in the solution of $\frac{1}{2} C_i Z_i^2$, wherein $C_i$ is the concentration of a certain ion in moles/liter, and $Z_i$ the charge of that ion. The required ionic strength may be obtained, for example, by adding from about 0.001 moles/liter to about 0.15 moles/liter of calcium chloride to the silica aquasol. Preferably the ionic strength is from about 0.015 to about 0.060, which corresponds to from about 0.005 to about 0.02 moles/liter when calcium chloride is used as the electrolyte.

In a typical hydrophilizing process of a thermoplastic fibrous web with positively charged silica, a thermoplastic fibrous web is saturated with positively charged silica aquasol under reduced pressure according to the method described hereinabove. The web is subsequently removed from the silica sol, the excess liquid is allowed to drain. When saturation is achieved with padding equipment excess aquasol is squeezed out by the rolls of the equipment. The web is then transferred to an aqueous solution of a cationic, crosslinkable polyelectrolyte wherein the web is soaked for about 1 to about 15 minutes, (or passed through a subsequent padding equipment containing the polyelectrolyte), drained, and dried in air. It is advantageous, but not mandatory, to heat the drying air to about 65° C.

The polyelectrolyte solution has a concentration of from about 0.5% to about 6%. The pH is from about 1 to about 7, preferably from about 4 to about 6. The ionic strength of the solution is from about 0.003 to about 0.45, preferably from about 0.015 to about 0.060.

Cationic polyelectrolytes are macromolecules containing cationic groups. Suitable examples are amido, imino and amino groups. The polyelectrolytes suitable for use in the present invention are crosslinkable, that is capable of forming intermolecular chemical bonds. This is achieved by incorporating cross-linking agents in the polyelectrolyte molecule. Styrene and diallyl phtalate are among the more common cross-linking agents. For use herein the polyelectrolytes must be water soluble.

Particularly suitable cationic crosslinkable polyelectrolytes are the cationic curable resins which are commercially available for use as wet strength additives in the paper industry. Typically these are melamine-formaldehyde, urea-formaldehyde or polyvinylamide resins. Specific examples thereof are the ionic, water-soluble vinylamide polymers having sufficient glyoxal-reactive amide substituents and —CH—OH—CHO substituents to be thermo-setting and wherein the ratio of the number of —CH—OH—CHO substituents to the number of glyoxal reactive amide substituents is in excess of 0.06:1. These resins are more fully disclosed in U.S. Pat. No. 3,556,932, issued Jan. 19, 1971 to Cescia, et al., which is incorporated herein by reference.

DETERMINATION OF USEFUL CAPACITY

The useful absorption capacities of fibrous webs can be determined by their water absorption and desorption behavior. The basic procedure and the design of the apparatus are described by Burgeni and Kapur, "Capillary Sorption Equilibria in Fiber Masses", *Textile Research Journal*, 37 (1967) 362, which publication is incorporated herein by reference.

The absorption apparatus consists of a horizontal capillary tube, approximately 120 cm long, connected by a valve to a fluid reservoir. The end of the tube is connected by tygon tubing to a glass funnel containing an ASTM 4–8 micron frit on which the absorbent web sample is placed. The glass frit funnel is mounted on a vertical pole. The height of the frit above the capillary tube determines the hydrostatic suction being exerted on the sample. In a typical absorption/desorption experiment the volume of absorbed water is determined as a function of hydrostatic suction, starting at 100 cm.

The water absorption properties of a web are not primarily determined by the absorption capacity under soaking conditions (hydrostatic pressure=0), but rather by its ability to soak up water in competition with another material such as a table top or skin (hydrostatic pressure<0). It has been found that absorption data at −25 cm $H_2O$ hydrostatic pressure and of dodecane at −12 cm dodecane pressure correlate well with liquid partition tested on a hard surface and with spill wipe-up performance under representative real life conditions i.e. with the useful capacity. This useful capacity can be calculated from the absorption/desorption isotherms. Due to hysteresis the absorbed volumes at −25 cm $H_2O$ are different for the absorption branch and the desorption branch. The useful capacity is defined as the mean value of the two.

A simplified test was developed to determine the useful capacity of an absorbent web. In this test, the absorbed volume at −25 cm is measured. Next, the frit containing the sample is lowered to zero hydrostatic pressure and the equilibrium value of sorbed volume measured. Then the frit is raised again to the 25 cm mark and the absorbed volume at −25 cm in the desorption mode is determined. It has been found that the amount of hysteresis (i.e., the difference in absorbed volume at −25 cm in the desorption mode and absorbed volume at −25 cm in the absorption mode) is a measure for the wicking properties of the web; the less hysteresis, the better the wicking properties.

EXAMPLE I

Treatment of Polypropylene Fibers with Positively Charged Silica

Melt blown polypropylene microfiber webs were formed in accordance with the process described in U.S. Pat. No. 3,978,185 to Buntin, et al. Fiber diameters were about 4 micrometers, web densities about 0.07 g/cm$^3$.

The polypropylene fiber webs were immersed in a 0.1% silica aquasol. The amount of sol was 100 ml per gram of web. The silica was a positively charged silica with particle size of 13–15 nm, overall silica:alumina ratio of about 13:2 (surface ratio about 1:1) (WESOL P from Wesolite Corp.). The sol was made by diluting the commercial concentrated sol (30%) with tap water having an ionic strength of about 0.024. The pH of the sol was adjusted to 3.5 with HCl. A vacuum of about 63 cm Hg (about 85×10$^3$ N/m$^2$) was exerted on the vessel containing the web and the sol to make sure that the web became fully saturated. The vacuum was released and the saturated web removed from the sol. The web was next placed in a 0.1% solution of PAREZ 631 NC at pH 6.0 (a polyacrylamide resin from American Cyanamid Co.) in tap water (ionic strength 0.024). After 10 minutes the web was removed from the solution, drained, and dried in a forced-air oven at 65° C. The web had excellent absorbent and wicking properties.

Similar polypropylene microfiber webs are treated the same way, except that the pH of the positively charged aquasol is adjusted to 2, 2.5, 3, 4, and 4.5, respectively. The resulting webs have excellent absorbent and wicking properties.

Samples of polypropylene fiber webs are treated as described above. The pH of the silica aquasol is adjusted to 3.5. The pH of the PAREZ solution is adjusted to 3, 4, 5 and 7, respectively. Webs having excellent absorbency and wicking properties are obtained.

EXAMPLE II

Treatment of Polyethylene Terephtalate Fibers with Positively Charged Silica

Melt blown polyethylene terephtalate microfiber webs were formed in accordance with the process described in U.S. Pat. No. 3,978,185 to Buntin, et al. Fiber diameters were about 4 micrometers, web densities about 0.07 g/cm³. The webs were treated with a 0.1% aquasol of WESOL P in tap water at pH 3.5 and/or a 0.1% solution of PAREZ 631 NC in tap water at pH 6 as described in Example I.

Samples of untreated polyethylene terephtalate microfibers and of fibers treated with WESOL P and PAREZ as described were studied under a scanning electron microscope at magnifications ranging from 5000X to 16,500X. Untreated fibers appeared to have a smooth surface. Treated fibers were covered with a continuous coating as evidenced by a microscopical surface roughness. The webs consisting of polyethylene terephtalate fibers covered with the continuous coating had excellent absorbency and wicking properties.

EXAMPLE III

The silica aquasols and cationic polyelectrolyte solutions as used in Examples I and II were made with tap water which had a hardness of about 21 grains/gallon, and an ionic strength of about 0.024. This experiment demonstrates the effect of ionic strength on the deposition of a continuous hydrophilic film on thermoplastic fibers. Melt blown polyester fiber webs were prepared as in Example I and treated with a 0.1% aquasol of WESOL P and a 0.1% solution of PAREZ 631 NC. The silica and polyelectrolyte treatments were carried out at varying ionic strength. The resulting webs were tested for absorption properties. The absorption data are given below.

| Water Source | Treatment % CaCl₂ added*/ | Ionic Strength | Sorption Capacities (ml/g) −25 cm ads. | soaking | −25 cm des. |
|---|---|---|---|---|---|
| Tap | 0 | 0.024 | 4.5 | 8.0 | 5.6 |
| Distilled | 0 | 0 | 0.4 | 9.1 | 6.4 |
| Distilled | 0.5 | 0.14 | 3.3 | 7.8 | 5.5 |
| Distilled | 0.1 | 0.027 | 3.2 | 8.7 | 6.0 |
| Distilled | 0.01 | 0.0027 | 0.5 | 8.5 | 5.9 |

*/Same concentration of CaCl₂ in both the silica aquasol and the polyelectrolyte solution.

The data demonstrate the dramatic effect of the ionic strength on the deposition of a continuous hydrophilic film.

EXAMPLE IV

This Example demonstrates the criticality of the nature of the polyelectrolyte used in the post treatment of the thermoplastic webs coated with positively charged silica. Melt blown polyethylene terephtalate webs were prepared and treated with WESOL P aquasol (in tap water) as described in Example I. After the saturation with positively charged silica aquasol, samples of the web were soaked for 5 minutes in 0.1% solutions of the following cationic materials: AlCl₃; poly(acrylamide); poly(ethylenimine); PAREZ 630 NC; and PAREZ 631 NC. The latter two are both crosslinkable cationic polyelectrolytes from American Cyanamide Co. PAREZ 630 NC probably has the formula

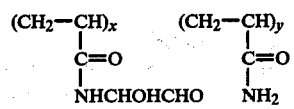

wherein x:y>0.06:1.
PAREZ 631 NC probably has the formula

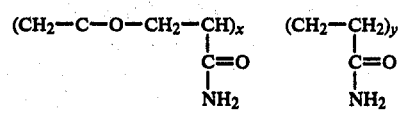

wherein x:y>0.06:1

Even though the two PAREZ formulas may not be exactly as depicted here, there is no doubt that both are crosslinkable cationic polyacrylamides. The adsorption characteristics of the samples were determined by means of the adsorption test described hereinabove. The rate of adsorption over the first 15 seconds of contact between the dry web and water at a hydrostatic pressure of −25 cm H₂O was monitored. This provides comparative data on wicking properties of the different samples. The results are given below.

| Post Treatment | Wicking ml/g.s | Sorption (ml/g) −25 cm ads | soaking | −25 cm des |
|---|---|---|---|---|
| AlCl₃ | 0.10 | 2.4 | 8.4 | 5.7 |
| Poly(acrylamide) | 0.11 | 2.4 | 8.4 | 5.6 |
| Poly(ethylenimine) | 0.05 | 1.4 | 9.9 | 7.0 |
| PAREZ 630 NC | 0.22 | 4.6 | 8.4 | 5.8 |
| PAREZ 631 NC | 0.17 | 5.0 | 8.5 | 6.3 |

The data demonstrate the importance of the use of a crosslinkable polyelectrolyte in the post treatment of fibers coated with positively charged silica, especially with respect to the wicking properties of the web. Since this is a post treatment, i.e., no deposition of silica takes place during this step, it is hypothesized that the crosslinkable cationic polyelectrolyte cooperates with previously deposited silica in the formation of a continuous hydrophilic film.

EXAMPLE V

Polyethylene terephtalate (PET) microfiber webs were formed in accordance with the process described in U.S. Pat. No. 3,978,185 to Buntin, et al. Fiber diameters were about 4 micrometers, web densities about 0.07 g/cm³. Sols with a concentration of 0.1% positively charged silica (WESOL P, see Example I) and pH=3.5 were prepared with tap water (ionic strength about 0.024) and with distilled water, respectively; also, 0.1% solutions of PAREZ 631 NC (see Example I) were prepared at pH=6 in tap water and in distilled water. Samples of PET webs were treated with either a tap water silica sol and a tap water solution of PAREZ 631 NC, or with a distilled water silica sol and a distilled water solution of the PAREZ, by the method described in Example I. After drying the webs were examined under a scanning electron microscope at magnifications ranging from 700X to 16,500X. The surface of untreated fibers was entirely smooth. The fibers treated with distilled water solutions appeared to be smooth, but partially covered with a flaky deposit. Fibers treated with tap water solutions appeared to be entirely covered with a continuous somewhat rough, coating. These observations clearly indicate that the treatment with a tap water sol of positively charged silica followed by a treatment with a tap water solution of a polyacrylamide resin results in a continuous coating. The samples thus treated were found to possess good wetting properties.

Criticality of Post Treatment

Melt blown polypropylene fiber webs were treated with WESOL P as described in Example I. Some samples were post treated with PAREZ as described in Example I; other sample did not receive post treatment. In one case the pH of the silicca aquasol was raised from 3.5 to 9 in an attempt to deposit silica on the fibers by flocculation. The wettability of the webs was determined as follows: a drop of distilled water was dropped upon the web; the wetting was visually determined and graded as follows: 0=no wetting; 1=slow wetting; 2=wetting with some hesitation; 3=immediate wetting. The results are given in Table I, below.

TABLE I

| Silica | | PAREZ 631 NC | | |
|---|---|---|---|---|
| Type | pH | Conc. (%) | pH | Wettability |
| WESOL P | 3.5 | No PAREZ | | 1 |
| WESOL P | 3.5 → 9 | No PAREZ | | 0 |
| WESOL P | 3.5 | 1.0 | 7.1 | 3 |
| WESOL P | 3.5 | 0.1 | 6.0 | 3 |
| WESOL P | 6.0 | 0.1 | 7.1 | 0 |

The data demonstrate the criticality of the post treatment with the cross-linkable cationic polyelectrolyte. The data further demonstrate the criticality of the pH of the positively charged silica aquasol.

Criticality of the post treatment was further demonstrated by the following test. Samples of polyethylene terephtalate, identical to the ones described in Example II were treated with a WESOL P aquasol in tap water at pH 3.5 and/or with a solution of PAREZ 631 NC in tap water at pH 6, according to the schedule given in the table below. The absorption properties of the webs were determined as described hereinabove. The results are given below.

| Treatment | | Sorption Capacities (ml/g) | | |
|---|---|---|---|---|
| Step 1 | Step 2 | −25 cm ads. | soaking | −25 cm des. |
| WESOL P | PAREZ | 5.0 | 9.1 | 6.2 |
| WESOL P | — | 4.4 | 9.5 | 6.7 |
| PAREZ | — | 0.3 | 9.3 | 6.7 |
| PAREZ | WESOL P | 0.4 | 8.2 | 5.8 |

The data demonstrate that post treatment with a cationic polyelectrolyte increases the sorption capacity in the absorption mode and therefore increases the useful capacity of webs treated in this way. The post treatment also reduces the absorption/desorption hysteresis, which indicates that such webs have improved wicking properties. This was confirmed by independent tests aimed at establishing the wicking properties of the webs. The data further show that the order of treatment is critical: pretreatment with the polyelectrolyte results in very poorly wetting webs, in fact, much poorer than obtained upon treatment with positively charged silica alone.

Coating of Hydrophilic Fibers

Coating of hydrophilic fibers with a continuous film comprising silica results in a significant improvement of the absorbent properties of webs made with such fibers. In particular, the wicking rate, i.e., the rate at which the web absorbs water, is increased when the fibers are coated; but also the absorption at −25 cm hydrostatic pressure is higher when such a coating is present.

For reasons of availability and cost, cellulose fibers are preferred for use in this embodiment of this invention. Suitable sources of cellulose fibers are wood pulp, abaca, wheat straw, rice straw, and the like. Positively charged silica is particularly suitable for use herein.

Coating of the fibers may be done prior to or subsequent to formation of a fibrous web. Formation of the web itself is not critical to this invention, and may be done by one of the techniques known in the art, i.e., wet laying, solvent laying or air laying. The continuous film is formed on the surface of the fibers upon contacting the fibers (or the fibrous web, as the case may be) with a bath containing the colloidal silica under proper conditions of pH and silica concentration. The weight ratio fibers:silica may vary from about 140:1 to about 10:1, preferably from about 40:1 to about 20:1. When preformed webs are contacted with a silica aquasol, it is convenient to use relatively concentrated sols, i.e., liquid:fiber ratios in the order of 100:1. But when the silica treatment is applied to fibers prior to web formation, it is generally more convenient to use liquid:fiber ratios in the order of 500:1 to 1000:1. The latter situation typically arises when silica treatment is carried out by adding a concentrated silica aquasol to a cellulose pulp of, e.g., 0.2% consistency. Although the concentration of the sol and the amount of liquid may vary within the limits discussed hereinabove, the two parameters must be such as to result in a silica/dry fiber ratio of from about 1:140 to about 1:10, preferably from about 1:40 to about 1:20.

The pH of the positively charged silica aquasol must be in the range of from about 2 to about 9, preferably from about 6 to about 8. When the silica treatment is carried out at a pH below 2, silica is in effect deposited on the fiber surface, but the silica fails to produce optimum absorbency.

The contact time is not critical and may vary from about 5 minutes to 10 hours or more, provided that when contact times of less than about 15 minutes are used the slurry or sol is agitated. In general, contact times can be shorter when the pH of the sol is above 4, particularly when the pH is above 6. At these pH values the sol is destabilized which increases the rate of deposition onto the fibers.

At a pH value of more than 9 the fibers develop an undesirable yellow color.

Particularly good results are obtained when the fibers are contacted with the sol at a pH of from about 3 to about 5 and the pH is then raised to about 8 in the presence of the fibers.

EXAMPLE VI

Abaca fiber drylap was defiberized in a hammer mill type disintegrator. A WESOL P aquasol of 0.1% strength was made up and its pH adjusted to 6.0. Abaca fibers were slurried in the sol (sol:fiber ratio=100:1, silica:fiber ratio=1:10). The slurry was allowed to equilibrate for about 16 hours. The fibers were formed into a dry lap. A web was formed from dry lap by air laying. The amount of Si in the sample was determined by atomic absorption to be 1.9%.

The resulting web was tested for absorption properties. As compared to untreated control, the silica treated web had a higher useful capacity. Also, absorption/desorption hysteresis was significantly less for the treated sample, indicating superior wicking properties.

EXAMPLE VII

Hardwood sulfite pulp fibers were dispersed in aquasols of positively charged silica (WESOL P) at pH 6. The sol:fiber weight ratio was 50:1 in each case, the silica concentrations were varied as to give silica:fiber ratios of 1:80, 1:40, 1:20 and 1:10. (In papermaking practice, such ratios are expressed in pounds per ton, a ton being 2000 lbs. The above ratios correspond to 25, 50, 100 and 200 lbs/ton, respectively). The fibers were equilibrated for one hour, then the silica sol was drained off and the fibers collected on a wire mesh screen. The resulting wet lap was dried at 65° C. for two hours. The dry fibers were air laid into webs of 0.10 g/cm$^3$ density. Webs coated with negatively charged silica were formed in substantially the same way. Coating of the fibers was done at pH=3.5; silica:fiber ratios were 25, 50 and 100 lbs/ton.

The webs were subjected to absorption testing. The water uptake during the first minute appeared to be linear. The slope of the plot amount absorbed vs. time is a measure of the wicking rate. Results are given below.

| Type Silica | Ratio lbs/ton | Wicking ml/g min | Sorption, ml/g −25 cm ads | soaking | −25 cm des |
|---|---|---|---|---|---|
| Control | 0 | 0.14 | 1.5 | 8.1 | 6.5 |
| Positive | 25 | 0.42 | 2.8 | 8.8 | 7.3 |
| Positive | 50 | 1.44 | 4.1 | 7.5 | 6.3 |
| Positive | 100 | 2.52 | 4.5 | 7.1 | 6.1 |
| Positive | 200 | 1.74 | 4.0 | 7.1 | 5.9 |
| Negative | 25 | 0.96 | 4.1 | 8.2 | 6.8 |
| Negative | 50 | 0.84 | 3.8 | 8.4 | 6.9 |
| Negative | 100 | 0.90 | 4.0 | 8.3 | 6.9 |

The data indicated that a continuous silica film on the fiber surface increases the useful capacity and the wicking rate of webs made with such fibers.

EXAMPLE VIII

A mixed softwood/hardwood (60/40/fiber pulp) was contacted with positively charged silica aquasol at pH 6 for five minutes under agitation. The pulp consistency was 0.1%. Two samples were made, one at a silica:fiber ratio of 15 lbs/ton, one at 200 lbs/ton. A third sample was contacted with negatively charged silica at pH 3.5 and silica:fiber ratio of 15 lbs/ton. The fibers were formed into a web by wet laying on a wire mesh screen. The webs were tested for wicking properties. All silica treated webs wicked water significantly faster than an untreated control sample.

EXAMPLE IX

Southern pine softwood drylap was mixed in a Waring blender with enough distilled water to form a 2% slurry. The pH was adjusted to 6, and enough of a concentrated WESOL P sol was added to obtain a silica concentration of 0.6%. The slurry was mixed for 3 minutes, then allowed to equilibrate for about 90 minutes. Handsheets of about 45 grams were formed on a Deckel box. The sheets were dried in an oven at about 65° C. and cut into strips of about 25 mm which were then defiberized. The fibers were formed into webs with a density of about 0.10 g/cm$^3$ and a basis weight of about 0.02 g/cm$^2$ by air laying. The webs wicked water significantly faster than control samples without silica. Additional webs were made by the same method, except that the silica treatment was carried out at pH values of 2, 4, 6 and 8, respectively. All samples wicked water significantly faster than control.

The samples treated at pH 8 were subjected to energy dispersive spectroscopic mapping. Silica appeared to be continuously distributed at 100 nm level of resolution.

Still other webs were made by the above method modified in that silica was added at pH 3.5, and the pH was subsequently raised to 8. The webs thus made wicked water significantly faster than webs which had been treated with silica at pH fixed at values of 2, 4, 6 and 8.

What is claimed is:

1. A hydrophilic absorbent fibrous web comprising thermoplastic polymer fibers which are coated with a continuous film consisting essentially of positively charged silica and a crosslinkable cationic polyelectrolyte.

2. A process for coating thermoplastic fibers with a continuous film comprising silica, said process comprising the step of immersing the fibers in a positively charged silica aquasol containing colloidal silica with average particle size in the range of from about 3 nm to about 150 nm, said aquasol having a pH of from about 1 to about 5 and an ionic strength of from about 0.003 to about 0.45, followed by the step of immersing the fibers in an aqueous solution of a water-soluble, cationic, crosslinkable polyelectrolyte, said solution having a pH of from about 1 to about 7 and an ionic strength of from about 0.003 to about 0.45.

3. The absorbent fibrous web of claim 1 wherein the crosslinkable cationic polyelectrolyte is a melamine-formaldehyde resin, a urea-formaldehyde resin or a polyvinylamide resin.

4. The process of claim 2 wherein the colloidal silica has an average particle size in the range of from about 3 nm to about 50 nm.

5. The process of claim 2 wherein the absolute air pressure over the silica aquasol is reduced to below 10 cm Hg.

6. The process of claim 2 wherein the concentration of the aqueous solution of the cationic polyelectrolyte is from about 0.5% to about 6%.

7. The process of claim 2 wherein the pH of the polyelectrolyte solution is from about 4 to about 6.

8. The process of claim 2 wherein the ionic strength of the polyelectrolyte solution is from about 0.015 to about 0.060.

9. The process of claim 2 wherein the cationic polyelectrolyte is a melamine-formaldehyde resin, a urea-formaldehyde resin or a polyvinylamide resin.

10. A process for coating hydrophilic fibers with a continuous film comprising silica, said process comprising the step of immersing the fibers in a silica aquasol containing from about 0.01% to about 2% positively charged colloidal silica, said aquasol having a pH of from about 2 to about 9, and the amount of aquasol being such as to result in a silica:fiber ratio of from about 1:40 to about 1:20.

11. A process according to claim 10 wherein the hydrophilic fibers are cellulose fibers.

12. A process according to claim 10 wherein the silica aquasol has a pH of from about 6 to about 8.

13. A process according to claim 10 wherein the fibers are immersed in a silica aquasol at a pH of about 3 and the pH is subsequently raised to about 8 in the presence of the fibers.

14. The product of the process of claim 2.

15. The product of the process of claim 10.

* * * * *